United States Patent [19]

Murphy, Jr. et al.

[11] Patent Number: 5,703,278
[45] Date of Patent: Dec. 30, 1997

[54] PRESSURIZED FLUID DENSITY BALANCE

[75] Inventors: Robert J. Murphy, Jr., Kingwood; James G. Anderson, Houston, both of Tex.

[73] Assignee: Fann Instrument Company, Houston, Tex.

[21] Appl. No.: 642,716

[22] Filed: May 3, 1996

[51] Int. Cl.$^6$ ................................................. G01N 9/00
[52] U.S. Cl. ........................ 73/30.01; 73/30.04; 73/433
[58] Field of Search ......................... 73/30.01, 30.04, 73/32 A, 433, 438

[56] References Cited

U.S. PATENT DOCUMENTS 3,747,415  7/1973  Nickles et al. .
4,095,473  6/1978  Batchelor ................................. 73/433
4,374,474  2/1983  Cain .

OTHER PUBLICATIONS

Fann Permeability Plugging Apparatus Instruction Manual Authored and published by Fann Instrument Co., P.O. Box 4350, Houston, Tx 77210 in 1995. (no month).
Halliburton Tru-Wate Cup Operating Instructions, 15 pages authored and published by Halliburton, P.O. Drawer 1431, Duncan, Ok 73536 before May 3, 1995.

Primary Examiner—Christine K. Oda
Attorney, Agent, or Firm—Browning Bushman

[57] ABSTRACT

A conventional fluid density balance beam measurement instrument used for measuring fluid density at atmospheric pressure is converted for use to measure fluid density at super-atmospheric pressure. The conversion is made without modifying the structure of the conventional instrument. A pressure lid, placed over the open mouth of the instrument's sample cup, is held in place by a removable retaining structure that wraps around the base of the cup. A screw ring at the top of the retainer applies a retaining pressure against the lid. Pressure is applied to the cup through a check valve stem extending through the lid. An adjustable flange on the rim of the lid permits the lid to advance into the cup to change the cup volume for sizing the cup to obtain a precisely known volume for measurement. A counterweight is removably connected to the balance beam to compensate for the weight added by the lid and retaining structure. A weight compartment in the counterweight permits the addition of small amounts of weight to calibrate the balance beam. The lid, retaining structure and counterweight are removable to return the instrument to its conventional configuration for normal atmospheric measurements.

15 Claims, 2 Drawing Sheets

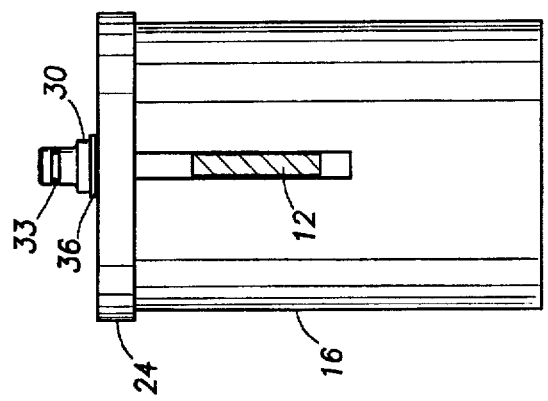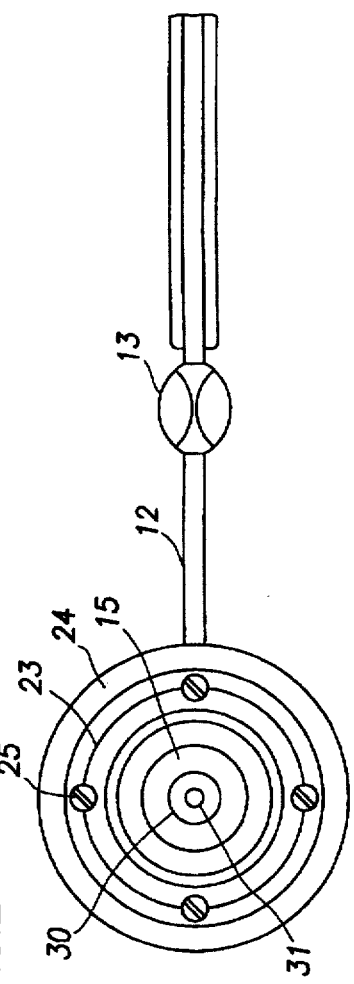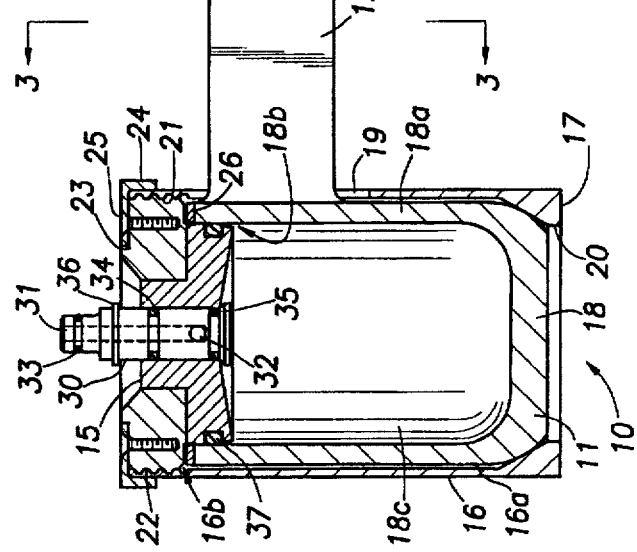

PRESSURIZED FLUID DENSITY BALANCE

FIELD OF THE INVENTION

The present invention relates generally to the measurement of fluid densities. More specifically, the present invention relates to a structure for modifying a conventional measurement instrument used at atmospheric pressure to an instrument that measures pressurized fluid for determining the density of the fluid in a pressurized environment.

BACKGROUND OF THE INVENTION

The density of fluids is commonly measured by placing a known volume of the fluid in a graduated balance beam scale and determining the weight of the known volume by moving a counterbalance indicator to the point required to exactly offset and thus balance the weight of the sample. The graduations at the point at which the counterbalance indicator stops gives the measure of the sample weight. The sample density is the measured weight divided by the known volume of the sample.

Some fluids have entrained gases that, at atmospheric pressure, occupy a significant volume within the sample. These same gases are compressed when the fluid is placed under pressure as may occur, for example, when the fluid resides at a subsurface location within a well. As a result, a given volume of fluid at atmospheric pressure may occupy a significantly smaller volume at the higher pressure encountered at its destined location.

To overcome this problem in density measurement, the fluid sample may be subjected to super-atmospheric pressure so that the entrained gases are compressed and occupy less volume. An improved measure of the density of these fluids is obtained with such pressurized measurements.

The instruments used for performing pressurized measurements have traditionally been relatively expensive. Moreover, many measurement applications do not require that the fluid be pressurized since the fluid may have no significant entrained gases. As a result, the lower cost atmospheric measurement instrument is commonly employed to perform all density measurements, including those that would be more accurately performed using a pressurized instrument.

BRIEF DESCRIPTION OF THE INVENTION

A conventional, atmospheric balance beam density measuring instrument is converted for use as a pressurized measuring instrument without any structural modification of the conventional instrument. As a result, the basic instrument may be employed as either an unpressurized or a pressurized measurement instrument.

The sample cup in a conventional instrument is pressurized by employing a specially configured lid that seals over the mouth of the cup. The lid is held in place as the sample is pressurized by a retaining structure that surrounds the lid and extends down and around the bottom of the cup. The design of the retaining structure is such that the base of the cup provides the reaction force for the force attempting to remove the lid from the pressurized sample chamber. A threaded area at the top of the retaining structure cooperates with a threaded retainer ting that can be tightened down onto the lid to apply a retaining force on the lid.

The lid itself is equipped with an annular flange section that is connected by threads to the main lid body. The flange rests on the top of the cup. The lid body may be advanced or retracted by threading into or unthreading from the flange to change the volume contained within the cup. This feature allows the cup volume to be adjusted so that a precisely known volume is contained within the enclosed chamber matching that contained in the atmospheric pressure instrument when it is capped with a conventional lid.

The enclosed chamber is pressurized through a combination access tube and check valve that allows the cup to be filled with the sample and pressurized using a conventional sample pump. When the sample fills the cup and is properly pressurized, the check valve is closed and the pump is removed so that the sample may be weighed.

A counterbalance is removably secured to the balance beam to counteract the added weight of the lid and retaining structure. A weight compartment on the counterweight permits small weights to be added or removed from the counterweight to precisely calibrate the instrument.

When normal atmospheric measurements are desired, the lid, retaining structure and counterbalance are removed to return the instrument to its original condition.

From the foregoing, it will be appreciated that a primary object of the present invention is to provide a pressurized fluid density balance beam measuring instrument using a conventional, unpressurized balanced beam measuring instrument.

Another object of the present invention is to provide a universal pressurized measuring adaption for a non-pressurized measuring instrument that will permit the volume in the confined sample chamber to be adjusted to compensate for variations in cup volume of the unpressurized instruments.

Another important object of the present invention is to provide a counterbalance that can be adjusted in weight as required to exactly offset the added weight of the lid and retaining structure used in pressurized measurements.

These and other features and advantages of the present invention will be more fully understood and appreciated by reference to the following drawings, specification and claims.

BRIEF DESCRIPTION OF THE DRAWINGS

FIG. 1 is a vertical elevation, partially in vertical section, illustrating a conventional unpressurized balance beam fluid density measuring instrument equipped with the pressure lid, retaining structure and counterweight of the present invention;

FIG. 2 is an overhead view of a portion of the apparatus of FIG. 1;

FIG. 3 is a vertical elevation, partially in section, taken along the line 3—3 of FIG. 1;

DETAILED DESCRIPTION OF THE PREFERRED EMBODIMENTS

Figure 8:
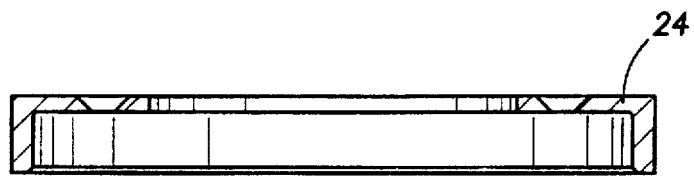
FIG. 8 is vertical sectional view illustrating details in the manual grip of the present invention.
Figure 7:
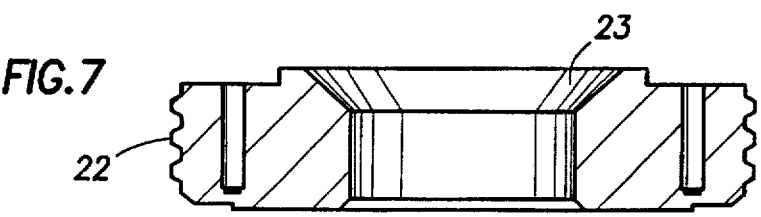
FIG. 7 is a vertical sectional view illustrating details in the construction of the retaining ring of the present invention.

The instrument of the present invention is indicated generally at 10 in FIG. 1. The instrument 10 is comprised of a conventional fluid receptacle cup 11, graduated balance beam 12, balance point 13 and sliding balance rider 14. The instrument 10 is employed to measure the weight of a given volume of fluid to thus determine the fluid density. The weight of the sample is obtained by sliding the balance rider 14 along the beam 12 until the balance beam is exactly balanced about the balance point 13. The beam 12 is marked with one or more graduations or scales (not illustrated) that display the fluid weight at the point the rider is positioned to obtain a balance. As thus far described, the instrument 10 functions in a conventional manner to provide the density of a fluid occupying the sample cup.

A density measurement of a pressurized fluid may be obtained by equipping the cup 11 with a pressure lid 15 that is held in place over the cup within the recess 16a of a retaining structure 16. As may be seen by joint reference to FIGS. 1 and 3, the structure 16 is also cup shaped with a retainer mouth 16b and a base section 17 that extends below a bottom area 18 of the cup 11. The cup 11 has a cylindrical wall structure 18a that extends from the bottom area 18 to a cup mouth 18b opening into a containment area 18c. The structure 16 has a slot 19 to receive the balance beam 12. The bottom of the structure 16 has a circular opening 20 to prevent retention of fluid or other extraneous material coming within the structure recess.

Threads 21 formed adjacent the retainer mouth 16b along the upper internal surface of the retainer structure 16 mate with threads 22 formed on the external circumferential end surface of a retainer ring 23. An annular grip ring 24 is connected to the retainer ring 23 by metal screws 25. The grip ring 24 lips over the outer surface of the support structure 16 to provide a manual gripping point for screwing the ring threads 22 into and out of engagement with the support structure threads 21 and to protect the underlying threads from contamination.

Figure 4:
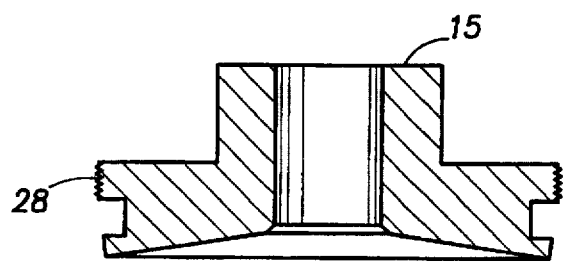
FIG. 4 is an assembly drawing in vertical section illustrating details in the construction of the pressure lid of the present invention.
Figure 5:
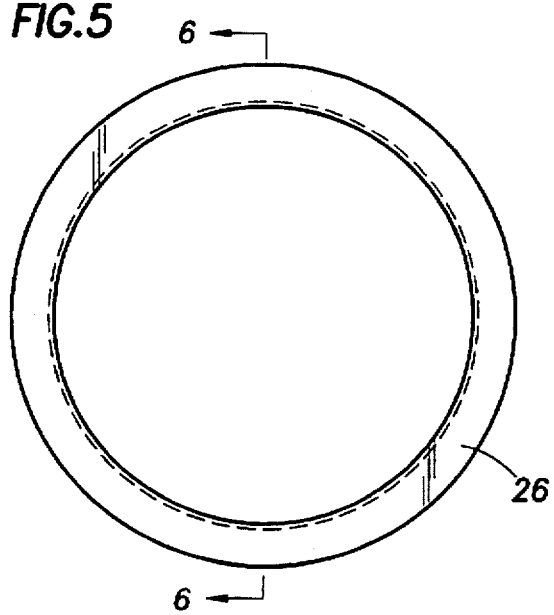
FIG. 5 is an overhead view of the adjustable flange of the present invention.
Figure 6:
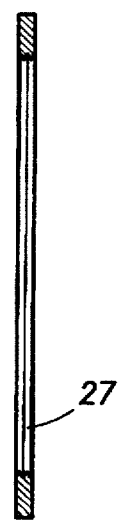
FIG. 6 is a cross-sectional view taken along the line 6—6 of FIG. 5 illustrating details in the construction of the flange of the present invention.

The lid 15 includes an adjustable flange 26 that is connected by threads 27 to threads 28 on the main lid body. The flange 26 supports the lid 15 over the mouth 18b of the cup 11. As illustrated best by joint reference to the component drawings of FIGS. 4, 5 and 6, the flange 26 is a narrow ring that is internally threaded with the threads 27 that are adapted to engage the external lid threads 28.

The adjustable flange 26 performs the important function of allowing the lid 15 to be advanced into or out of the cup 11 to change the volume of fluid that may be contained within the cup 11 when the pressurized sample is being measured. This capability allows the pressure containing chamber area 18c of the instrument 10 to compensate for variations in different sample cup structures. Once the proper position is obtained for a specific receptacle cup, the flange may be permanently bonded to the lid.

A central check valve filler assembly 30 extends through the lid 15 to provide fluid and pressure to the enclosed cup. The assembly 30 has a central bore 31 that communicates with radial ports 32.

Resilient o-ring seals 33, 34 and 35 are disposed on the assembly 30 to seal with connecting structure as will be described. A snap ring retainer 36 holds the assembly in place within the lid 15. The lid 15 is sealed against the internal surface of the mouth 18b of the cup 11 by an o-ring seal 37.

The opposite end of the balance beam 12 is equipped with a cylindrical counterweight balance that is used to offset the weight of the lid 15 and retaining structure 16. A rod tip 39 at the end of the beam 12 extends through a bore 40 formed through the counterweight 38. A set screw 41 holds the counterweight 38 in secure engagement with the rod 14. A second bore 42 capped by a threaded plug 43 is provided in the counterweight 38 to hold small weighting elements, such as lead shot, for calibrating the instrument.

In operation, a measured volume of fluid is initially placed in the receptacle cup 11, the lid 15 is placed over the cup and the lid is then rotated through the flange 26 until the fluid is displaced from the cup to reach a predetermined level relative to the lid. At this point, the enclosed cup volume in the area 18c is configured to contain exactly the same measured volume of the sample fluid. The flange and lid may be bonded at this configuration if the pressurizing structure is to be consistently employed with the same cup.

With the sample fluid in the calibrated cup 11, the lid is placed over the cup and the retaining ring 23 is placed over the lid. The ring 23 is rotated to engage the threads 21 and 22 causing the ring to advance toward the base section 17 of the retaining structure 16 to impose a restraining force on the lid that will keep the flange 26 firmly engaged with the top of the cup 11 to prevent any pressure induced lid movement that would change the volume of the contained sample area. Additional fluid is added to the cup 11 through the assembly 30 by a conventional pump device (not illustrated) that telescopes over the assembly and seals with the o-ring 33. During the fluid addition and pressurizing procedure, the assembly 30 is moved down into the cup area until the retainer ring 36 engages the top of the lid 15. At this point, the radial ports 32 of the assembly 30 opens into the cup so that pressurized fluid may flow from the pump through the central bore 31 and out of the radial bore 32 into the cup 11. The seal 34 prevents pressure loss around the assembly 30. When the cup 11 is properly filled and pressurized, the assembly 30 is allowed to return to the position illustrated in FIG. 1 and the pump is removed. As will be understood, the o-rings 34 and 35 cooperate with the assembly 30 to seal the opening through the lid and retain the pressure in the cup 11. The pressure of the fluid within the cup acts against the assembly 30 to maintain the assembly in its upper, sealed position. Once the pump is removed, the sample is weighed to determine the true density of the fluid.

From the foregoing, it will be appreciated that the described modification of a conventional density balance instrument requires no permanent structural modification of the instrument so that it may be returned to normal, non-pressurized uses. The adjustment feature of the invention also permits the modification to be performed while compensating for variations in volume containment occurring from one instrument to another. The modification provided by the present invention also economically permits pressurized measurement to be obtained using existing, conventional instruments.

The foregoing disclosure and description of the invention is illustrative and explanatory thereof. It will be appreciated by those skilled in the art that various changes in the size, shape and materials, as well as in the details of the illustrated construction. The combinations of features and the method steps discussed herein may be made without departing from the spirit of the invention.

What is claimed is:

1. A pressurizable fluid balance instrument comprising:
    a receptacle having a containment area defined by a bottom area, a wall structure and an opening into said containment area;

a pressure lid for closing said opening to form a pressure tight seal with said wall structure whereby said containment area may be pressurized to a pressure value above that existing externally of said containment area; and a retaining structure having a base section, said retaining structure extending independently of said wall structure between said pressure lid and said base section for transmitting pressure induced forces tending to unseal said lid from said wall structure to said bottom area whereby said lid retains a pressure seal with said wall structure.

2. A pressurizable fluid balance instrument as defined in claim 1, further comprising volume adjustment structure connected with said lid for changing the volume contained within said containment area when said lid is engaged with said wall structure.

3. A pressurizable fluid balance instrument as defined in claim 1, comprising:

a pressurizing connecting structure for communicating pressure into said containment area through said lid while said lid is closing said opening; and a one-way flow structure connected with said pressurizing structure for allowing fluid flow into said containment area and preventing fluid flow from said containment area.

4. A pressurizable fluid balance instrument as defined in claim 1, further comprising:

a balance arm connected to said receptacle; and an adjustable calcalibrating said connected with said balance arm for calibrating said instrument when said lid and retaining structure are connected to said receptacle.

5. A pressurizable fluid balance instrument as defined in claim 4, wherein said calibration device comprises a weight securing device for securing material of different weight to said balance arm as required to calibrate said instrument.

6. A pressurizable fluid balance instrument as defined in claim 1, wherein said retaining structure comprises:

a cup-shaped structure having a mouth and a recess for receiving said receptacle:

cup threads formed adjacent the mouth of said cup-shaped structure;

a retaining ring having circumferential threads for engagement with said cup threads, said ring being movable through threaded engagement with said cup threads to advance toward said receptacle bottom area for applying a retaining force exerted on said lid by said retaining structure.

7. A pressurizable fluid balance instrument as defined in claim 2, wherein said adjustment structure comprises a flange threadedly engaged with said lid, said flange being engageable with said wall structure whereby threaded movement of said lid toward said base section reduces the volume of said containment area.

8. A pressurizable fluid balance instrument as defined in claim 4, wherein said calibration device is removably secured to said balance arm whereby said instrument may be employed as an atmospheric density measurement instrument when said lid and retaining structure are removed from said receptacle.

9. A pressurizable fluid balance instrument as defined in claim 2, further comprising:

a balance arm connected to said receptacle; and an adjustable calibration device connected with said balance arm for calibrating said instrument when said lid and retaining structure are connected to said receptacle.

10. A pressurizable fluid balance instrument as defined in claim 9, wherein said calibration device is removably secured to said balance arm whereby said instrument may be employed as an atmospheric density measurement instrument when said lid and retaining structure are removed from said receptacle.

11. A pressurizable fluid balance instrument as defined in claim 4, wherein said calibration device is removably secured to said balance arm whereby said instrument may be employed as an atmospheric density measurement instrument when said lid and retaining structure are removed from said receptacle.

12. A pressurizable fluid balance instrument as defined in claim 8, further comprising volume adjustment structure connected with said lid for changing the volume contained within said containment area when said lid is engaged with said wall structure.

13. A pressurizable fluid balance instrument as defined in claim 6, further comprising volume adjustment structure connected with said lid for changing the volume contained within said containment area when said lid is engaged with said wall structure.

14. A pressurizable fluid balance instrument as defined in claim 13, wherein said calibration device comprises a weight securing device for securing material of different weight to said balance arm as required to calibrate said instrument.

15. A pressurizable fluid balance instrument as defined in claim 14, wherein said retaining structure comprises:

a cup-shaped structure having a mouth and a recess for receiving said receptacle;

cup threads formed adjacent the mouth of said cup-shaped structure;

a retaining ring having circumferential threads for engagement with said cup threads, said ring being movable through threaded engagement with said cup threads to advance toward said receptacle bottom area for applying a retaining force exerted on said lid by said retaining structure.

* * * * *

UNITED STATES PATENT AND TRADEMARK OFFICE
CERTIFICATE OF CORRECTION

PATENT NO. : 5,703,278
DATED : December 30, 1997
INVENTOR(S) : Robert J. Murphy, Jr.; James G. Anderson It is certified that error appears in the above-indentified patent and that said Letters Patent is hereby corrected as shown below:

In column 5, line 30, delete "calcalibrating said" and insert therefor --calibration device--.

Signed and Sealed this

Third Day of March, 1998

*Attest:*

BRUCE LEHMAN

*Attesting Officer*  Commissioner of Patents and Trademarks